(12) United States Patent
Dieterle et al.

(10) Patent No.: US 7,157,597 B2
(45) Date of Patent: Jan. 2, 2007

(54) HETEROGENEOUSLY CATALYZED PARTIAL GAS PHASE OXIDATION OF ACROLEIN TO ACRYLIC ACID

(75) Inventors: Martin Dieterle, Mannheim (DE); Jochen Petzoldt, Mannheim (DE); Heiko Arnold, Nanjing (CN); Wilhelm Ruppel, Mannheim (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 463 days.

(21) Appl. No.: 10/803,897

(22) Filed: Mar. 19, 2004

(65) Prior Publication Data
US 2004/0249196 A1 Dec. 9, 2004

Related U.S. Application Data

(60) Provisional application No. 60/475,792, filed on Jun. 5, 2003.

(30) Foreign Application Priority Data
Mar. 25, 2003 (DE) .............................. 103 13 214

(51) Int. Cl.
*C07C 51/235* (2006.01)
(52) U.S. Cl. ..................................... 562/535
(58) Field of Classification Search ...................... None
See application file for complete search history.

(56) References Cited

U.S. PATENT DOCUMENTS

| 6,403,829 B1 | 6/2002 | Unverricht et al. |
| 2004/0192963 A1 | 9/2004 | Dieterle et al. |
| 2004/0192964 A1 | 9/2004 | Petzoldt et al. |
| 2004/0192965 A1 | 9/2004 | Petzoldt et al. |
| 2004/0225158 A1 | 11/2004 | Dieterle et al. |
| 2004/0242926 A1 | 12/2004 | Dieterle et al. |

FOREIGN PATENT DOCUMENTS

| DE | 199 10 508 | 9/2000 |
| EP | 1 055 662 | 11/2000 |
| EP | 1 106 598 | 6/2001 |
| WO | WO 00/53559 | 9/2000 |

OTHER PUBLICATIONS

U.S. Appl. No. 10/912,075, filed Aug. 6, 2004, Schliephake et al.
U.S. Appl. No. 10/803,897, filed Mar. 19, 2004, Dieterle et al.
U.S. Appl. No. 10/934,624, filed Sep. 7, 2004, Borgmeier et al.
U.S. Appl. No. 10/920,428, filed Aug. 18, 2004, Borgmeier et al.

*Primary Examiner*—Paul A. Zucker
(74) *Attorney, Agent, or Firm*—Oblon, Spivak, McClelland, Maier & Neustadt, P.C.

(57) ABSTRACT

In a process for heterogeneously catalyzed partial gas phase oxidation of acrolein to acrylic acid, the starting reaction gas mixture is oxidized over a fixed catalyst bed 1 which consists of at least two fixed catalyst bed zones and is accommodated in two successive temperature zones A, B, and the transition from temperature zone A to temperature zone B does not coincide with a transition from one fixed catalyst bed zone to another fixed catalyst bed zone.

19 Claims, No Drawings

HETEROGENEOUSLY CATALYZED PARTIAL GAS PHASE OXIDATION OF ACROLEIN TO ACRYLIC ACID

This application is a non-provisional application of provisional application Ser. No. 60/475,792, filed Jun. 5, 2003, which in turn finds basis of priority in German application Ser. No. 103 13 214.7 filed Mar. 25, 2003.

The present invention relates to a process for partially oxidizing acrolein to acrylic acid in the gas phase under heterogeneous catalysis by conducting a starting reaction gas mixture which comprises acrolein, molecular oxygen and at least one inert gas, and contains the molecular oxygen and the acrolein in a molar $O_2:C_3H_4O$ ratio of $\geq 0.5$, in a reaction stage over a fixed catalyst bed whose active composition is at least one multimetal oxide comprising the elements Mo and V, in such a way that the fixed catalyst bed is arranged in two spatially successive temperature zones A, B, both the temperature of temperature zone A and the temperature of temperature zone B are a temperature in the range from 230 to 320° C., the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone, the temperature zone A extends up to a conversion of the acrolein of from 45 to 85 mol %, on single pass of the starting reaction gas mixture through the entire fixed catalyst bed, the acrolein conversion is $\geq 90$ mol % and the selectivity of acrylic acid formation based on converted acrolein is $\geq 90$ mol %, the sequence in time in which the reaction gas mixture flows through the temperature zones A, B corresponds to the alphabetic sequence of the temperature zones, the hourly space velocity of the acrolein contained in the starting reaction gas mixture on the fixed catalyst bed is $\geq 70$ l (STP) of acrolein/l of fixed bed catalyst ·h, and the difference $T^{maxA}-T^{maxB}$, formed from the highest temperature $T^{maxA}$ which the reaction gas mixture has within temperature zone A, and the highest temperature $T^{maxB}$ which the reaction gas mixture has within temperature zone B is $\geq 0°$ C.

The abovementioned process for partially oxidizing acrolein to acrylic acid under heterogeneous catalysis is known in principle, for example, from DE-A 19910508 and is particularly important as the second oxidation stage in the preparation of acrylic acid by two-stage catalytic gas phase oxidation starting from propene. Acrylic acid is an important monomer which finds use as such or in the form of its acrylic ester for obtaining polymers suitable, for example, as adhesives.

In addition to molecular oxygen and the reactants, the starting reaction gas mixture contains inert gas in order to keep the reaction gas outside the explosion range, among other reasons.

One objective of such a heterogeneously catalyzed partial gas phase oxidation of acrolein to acrylic acid is to achieve a very high selectivity $S^{AA}$ for acrylic acid (this is the number of moles of acrolein converted to acrylic acid, based on the number of moles of converted acrolein) on single pass of the reaction gas mixture through the reaction stages under otherwise predefined boundary conditions.

A further objective is to achieve a very high conversion $C^{AC}$ of acrolein (this is the number of moles of acrolein converted, based on the number of moles of acrolein used) on single pass of the reaction gas mixture through the reaction stages under otherwise identical boundary conditions.

When the $S^{AA}$ is high at high $C^{AC}$, this corresponds to a high yield $Y^{AA}$ of acrylic acid ($Y^{AA}$ is the product $C^{AC \cdot S^{AA}}$; i.e. the number of moles of acrolein converted to acrylic acid, based on the number of moles of acrolein used).

A further objective of such a heterogeneously catalyzed partial gas phase oxidation of acrolein to acrylic acid is to achieve a very high space-time yield ($STY^{AA}$) of acrylic acid (in a continuous process, this is the total amount of acrylic acid obtained per hour and unit volume of the fixed catalyst bed used in liters).

At a constant given yield $Y^{AA}$, the greater the hourly space velocity of acrolein on the fixed catalyst bed of the reaction stage (this refers to the amount of acrolein in liters at STP (=l (STP); the volume in titers which would be taken up by the appropriate amount of acrolein under standard conditions, i.e. at 25° C. and 1 bar) which is conducted as a constituent of the starting reaction gas mixture through one liter of fixed catalyst bed per hour), the higher the space-time yield.

DE-A 19910508 and WO 00/53559 teach that the abovementioned aims can indeed be achieved in principle by means of the process described at the outset for heterogeneously catalyzed partial gas phase oxidation of acrolein to acrylic acid. This is advantageous in that a relatively low volume-specific activity can be achieved within a fixed catalyst bed or fixed catalyst bed zone, for example, by diluting the actual shaped catalyst bodies bearing the active composition with inert shaped diluent bodies free of active composition, which makes the fixed catalyst bed less expensive overall.

However, a disadvantage of the teachings of DE-A 19910508 and WO 00/53559 is that they have no appropriate implementation example and thus leave open the specific configuration of such a procedure.

In a similar manner, EP-A 1106598 teaches a process for heterogeneously catalyzed partial gas phase oxidation of acrolein to acrylic acid, in which the fixed catalyst bed of the reaction stage consists of a plurality of spatially successive fixed catalyst bed zones whose volume-specific activity is substantially constant within one fixed catalyst bed zone and increases sharply in the flow direction of the reaction gas mixture at the transition from one fixed catalyst bed zone to another fixed catalyst bed zone and may be arranged in a plurality of temperature zones.

According to the teaching of EP-A 1106598, it is advantageous when fixed catalyst bed zones and temperature zones spatially coincide.

However, detailed in-house investigations have shown that spatial coincidence of fixed catalyst bed zones and temperature zones is generally not beneficial for optimum achievement of the different objectives referred to.

Among other factors, this can be attributed to the transition from temperature zone A to temperature zone B and the transition from one fixed catalyst bed zone to another fixed catalyst bed zone being taken as substantially coactive or as substantially counteractive measures.

When they are taken at substantially coactive measures (for example, transition from a colder temperature zone A to a hotter temperature zone B and transition from a fixed catalyst bed zone having lower volume-specific activity to a fixed catalyst bed zone having higher volume-specific activity; both measures have the purpose of supporting the reaction), the overall effect achieved in the transition region frequently overshoots the aim pursued and this results, for example, in a reduction of $S^{AA}$.

When they are taken as substantially counteractive measures (for example, transition from a hotter temperature zone A to a colder temperature zone B and transition from a fixed catalyst bed zone having lower volume-specific activity to a fixed catalyst bed zone having higher volume-specific activity; the first measure has the purpose of reducing the reaction, the second measure has the purpose of supporting the reaction), the individual effects frequently neutralize each other in the transition region, resulting in a reduced $C^{AC}$.

It is an object of the present invention to provide a process for heterogeneously catalyzed partial gas phase oxidation of acrolein to acrylic acid in a multizone arrangement, which does not have the disadvantages of the prior art.

We have found that this object is achieved by a process for partially oxidizing acrolein to acrylic acid in the gas phase under heterogeneous catalysis by conducting a starting reaction gas mixture comprising acrolein, molecular oxygen and at least one inert gas, and contains the molecular oxygen and the acrolein in a molar $O_2:C_3H_4O$ ratio of $\geq 0.5$ in a reaction stage over a fixed catalyst bed whose active composition is at least one multimetal oxide comprising the elements Mo and V, in such a way that the fixed catalyst bed is arranged in two spatially successive temperature zones A, B, both the temperature of temperature zone A and the temperature of temperature zone B are a temperature in the range from 230 to 320° C., the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone, the temperature zone A extends up to a conversion of the acrolein of from 45 to 85 mol %, on single pass of the starting reaction gas mixture through the entire fixed catalyst bed, the acrolein conversion is $\geq 90$ mol % and the selectivity of acrylic acid formation based on converted acrolein is $\geq 90$ mol %, the sequence in time in which the reaction gas mixture flows through the temperature zones A, B corresponds to the alphabetic sequence of the temperature zones, the hourly space velocity of the acrolein contained in the starting reaction gas mixture on the fixed catalyst bed is $\geq 70$ l (STP) of acrolein/l of fixed bed catalyst·h, and the difference $T^{maxA} - T^{maxB}$, formed from the highest temperature $T^{maxA}$ which the reaction gas mixture has within temperature zone A, and the highest temperature $T^{maxB}$ which the reaction gas mixture has within temperature zone B is $\geq 0°$ C., wherein the transition from temperature zone A to temperature zone B in fixed catalyst bed 1 does not (spatially) coincide with a transition from one fixed catalyst bed zone to another fixed catalyst bed zone.

In this document, the temperature of a temperature zone refers to the temperature of the portion of the fixed catalyst bed disposed in the temperature zone when practicing the process according to the invention, except in the absence of a chemical reaction. When this temperature is not constant within the temperature zone, the term temperature of a temperature zone then refers to the (numerical) mean of the temperature of the fixed catalyst bed along the reaction zone. It is essential that the heating of the individual temperature zones is substantially independent.

Since the heterogeneously catalyzed partial gas phase oxidation of acrolein to acrylic acid is a distinctly exothermic reaction, the temperature of the reaction gas mixture on reactive pass through the fixed catalyst bed is generally different from the temperature of a temperature zone. It is normally above the temperature of the temperature zone and generally passes through a maximum (heating point maximum) or falls starting from a maximum value within a temperature zone.

In general, the difference $T^{maxA} - T^{maxB}$ in the process according to the invention will not be more than 75° C. According to the invention, $T^{maxA} - T^{maxB}$ is preferably $\geq 3°$ C. and $\leq 60°$ C. With very particular preference, $T^{maxA} - T^{maxB}$ in the process according to the invention is $\geq 5°$ C. and $\leq 40°$ C.

When practicing the process according to the invention in the case of relatively low ($\geq 70$ l (STP)/l·h and $\leq 150$ l (STP)/l·h) catalyst velocities of acrolein on the fixed catalyst bed, the $T^{maxA} - T^{maxB}$ differences required according to the invention are normally attained when, on the one hand, both the temperature of reaction zone A and the temperature of reaction zone B are in the range from 230 to 320° C. and, on the other hand, the difference between the temperature of reaction zone B ($T_B$) and the temperature of reaction zone A ($T_A$), i.e., $T_B - T_A$, is $\leq 0°$ C. and $\geq -20°$ C. or $-10°$ C. or $\leq 0°$ C. and $\geq -5°$ C., or frequently $\leq 0°$ C. and $\geq -3°$ C.

When practicing the process according to the invention under increased acrolein catalyst velocities ($\geq 150$ l (STP)/l·h and $\leq 300$ l (STP)/l·h, or $\leq 600$ l (STP)/l·h), the $T^{maxA} - T^{maxB}$ differences required according to the invention are normally attained when, on the one hand, both the temperature of reaction zone A and the temperature of reaction zone B are in the range from 230 to 320° C. and $T_B - T_A$ is $>0°$ C. and $\leq 40°$ C., or $\geq 5°$ C. and $\leq 35°$ C. or 30° C., or $\geq 10°$ C. and $\leq 25°$ C. or 20° C., or 15° C.

The above statement regarding the $T_B - T_A$ temperature differences regularly also applies when the temperature of reaction zone A is within the preferred range of from 250 to 300° C. or in the particularly preferred range of from 260 to 280° C.

The hourly space velocity of acrolein on the fixed catalyst bed in the process according to the invention may therefore be, for example, $\geq 70$ l (STP)/l·h or $\geq 90$ l (STP)/l·h and $\leq 300$ l (STP)/l·h, or $\geq 110$ l (STP)/l·h and $\leq 280$ l (STP)/l·h, or $\geq 130$ l (STP)/l·h and $\leq 260$ l (STP)/l·h, or $\geq 150$ l (STP)/l·h and $\leq 240$ l (STP)/l·h, or $\geq 170$ l (STP)/l·h and $\leq 220$ l (STP)/l·h, or $\geq 190$ l (STP)/l·h and $\leq 200$ l (STP)/l·h.

According to the invention, temperature zone A preferably extends up to an acrolein conversion of from 50 to 85 mol % or from 60 to 85 mol %.

The working pressure in the process according to the invention can be either below atmospheric pressure (e.g. down to 0.5 bar) or above atmospheric pressure. Typically, the working pressure will be at values of from 1 to 5 bar, frequently from 1 to 3 bar. Normally, the reaction pressure will not exceed 100 bar.

According to the invention the molar $O_2$:acrolein ratio in the starting reaction gas mixture has to be $\geq 0.5$. It will frequently be at values of $\geq 1$. Typically, this ratio will be at values of $\geq 3$. According to the invention, the molar $O_2$:acrolein ratio in the starting reaction gas mixture is frequently from 1 to 2, or from 1 to 1.5.

In general, the acrolein conversion based on single pass in the process according to the invention may be ≧92 mol %, or ≧94 mol %, or ≧96 mol %, or ≧98 mol % and frequently even ≧99 mol %. The selectivity of acrylic acid formation will regularly be ≧92 mol %, or ≧94 mol %, frequently ≧95 mol % or ≧96 mol % or ≧97 mol %.

Useful catalysts for the fixed catalyst bed of the catalytic oxidation of acrolein in the gas phase according to the invention are all of those whose active composition is at least one multimetal oxide comprising Mo and V. Such suitable multimetal oxide catalysts can, for example, be taken from U.S. Pat. No. 3,775,474, U.S. Pat. No. 3,954,855, U.S. Pat. No. 3,893,951 and U.S. Pat. No. 4,339,355. Also particularly suitable are the multimetal oxide compositions of EP-A 427508, DE-A 2909671, DE-C 3151805, DE-B 2626887, DE-A 4302991, EP-A 700893, EP-A 714700 and DE-A 19736105, and also DE-A 10046928.

Suitable in this context are also the exemplary embodiments of EP-A 714700 and also of DE-A 19736105.

A multiplicity of the multimetal oxide active compositions suitable for the fixed catalyst bed, for example those of DE-A 19815281, can be encompassed by the general formula IV

$$Mo_{12}V_aX^1_bX^2_cX^3_dX^4_eX^5_fX^6_gO_n \qquad (IV)$$

where the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g from 0 to 40 and
n=a number which is determined by the valency and frequency of the elements in IV other than oxygen.

Embodiments among the active multimetal oxides IV which are preferred according to the invention are those which are encompassed by the following definitions of the variables of the general formula IV:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in IV other than oxygen.

However, multimetal oxides IV which are very particularly preferred according to the invention are those of the general formula V

$$Mo_{12}V_{a'}Y^1_{b'}Y^2_{c'}Y^5_{f'}Y^6_{g'}O_{n'} \qquad (V)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in V other than oxygen.

The multimetal oxide active compositions (IV) which are suitable according to the invention are obtainable in a manner known per se, for example disclosed in DE-A 4335973 or in EP-A 714700.

In principle, multimetal oxide active compositions, in particular those of the general formula IV, suitable for the catalysts of the fixed catalyst bed can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions IV include those compounds which are already oxides and/or those compounds which can be converted to oxides by heating, at least in the presence of oxygen.

The starting compounds for preparing multimetal oxide compositions IV can be intimately mixed in dry or in wet form. When they are mixed in dry form, the starting compounds are advantageously used as finely divided powder and subjected to calcining after mixing and optional compaction. However, preference is given to intimate mixing in wet form.

This is typically done by mixing the starting compounds in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, in particular those of the general formula IV, are generally used in the fixed catalyst bed not in powder form, but rather shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is advantageous. It will be appreciated that the supported catalyst may also have spherical geometry and the spherical diameter may be from 2 to 10 mm.

It will be appreciated that the pulverulent active composition or its pulverulent precursor composition which is yet to be calcined can also be shaped by applying to preshaped inert catalyst supports. The coating of the support bodies to prepare the coated catalysts is generally performed in a suitable rotatable vessel, as disclosed, for example, by DE-A 2909671, EP-A 293859 or EP-A 714700.

To coat the support bodies, the powder composition to be applied is advantageously moistened and is dried again after application, for example by means of hot air. The coating thickness of the powder composition applied to the support body is advantageously selected within the range from 10 to 1 000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders having a grit layer. It is suitable to use substantially nonporous, surface-roughened, spherical supports made of steatite (e.g. Steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). It will be appreciated that the fineness of the catalytically active oxide compositions to be applied to the surface of the support body is adapted to the desired coating thickness (cf. EP-A 714 700).

Advantageous multimetal oxide active compositions to be used for the catalysts of the fixed catalyst bed are also compositions of the general formula VI $$[D]_p[E]_q \quad (VI)$$

where the variables are defined as follows:
$D = Mo_{12}V_{a''}Z^1_{b''}Z^2_{c''}Z^3_{d''}Z^4_{e''}Z^5_{f''}Z^6_{g''}O_{x''}$,
$E = Z^7_{12}Cu_{h''}H_{i''}O_{y''}$,
$Z^1$ = W, Nb, Ta, Cr and/or Ce,
$Z^2$ = Cu, Ni, Co, Fe, Mn and/or Zn,
$Z^3$ = Sb and/or Bi,
$Z^4$ = Li, Na, K, Rb, Cs and/or H,
$Z^5$ = Mg, Ca, Sr and/or Ba,
$Z^6$ = Si, Ali Ti and/or Zr,
$Z^7$ = Mo, W, V, Nb and/or Ta, preferably Mo and/or W
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements in VI other than oxygen and p,q=numbers other than zero whose p/q ratio is from 160:1 to 1:1, and which are obtainable by separately preforming a multimetal oxide composition E $$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$, which comprises the abovementioned elements in the stoichiometry D $$Mo_{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions VI in which the preformed solid starting composition 1 is incorporated into an aqueous starting composition 2 at a temperature of <70° C. A detailed description of the preparation of multimetal oxide VI catalysts is contained, for example, in EP-A 668104, DE-A 19736105, DE-A 10046928, DE-A 19740493 and DE-A 19528646.

With regard to the shaping, the statements made for the multimetal oxide IV catalysts apply to the multimetal oxide VI catalysts.

Further suitable multimetal oxide compositions for the catalysts of the fixed catalyst bed are those of DE-A 19815281, in particular all exemplary embodiments from this document. With regard to the shaping, the same applies as was stated above.

For the fixed catalyst bed of the process according to the invention, particularly suitable catalysts are the coated catalysts S1 (stoichiometry: $Mo_{12}V_3W_{1.2}Cu_{2.4}O_n$) and S7 (stoichiometry: $Mo_{12}V_3W_{1.2}Cu_{1.6}Ni_{0.8}O_n$) from DE-A 4442346 having an active composition fraction of 27% by weight and a coating thickness of 230 μm, the coated catalyst from preparative example 5 of DE-A 10046928 (stoichiometry: $Mo_{12}V_3W_{1.2}Cu_{2.4}O_n$) having an active composition fraction of 20% by weight, the coated catalysts of examples 1 to 5 from DE-A 19815281, but equally the above-mentioned coated catalysts for the second reaction stage applied to support rings of geometry 7 mm×3 mm×4 mm (external diameter×length×internal diameter) having an active composition fraction of 20% by weight (based on the overall composition of the coated catalyst), and also a coated catalyst having a biphasic active composition of stoichiometry $(Mo_{10.4}V_3W_{1.2}O_x)(CuMo_{0.5}W_{0.5}O_4)_{1.6}$ and prepared according to DE-A 19736105 and having an active composition fraction of 20% by weight applied to the abovementioned 7 mm×3 mm×4 mm support.

The catalysts recommended above for the reaction stage according to the invention are also suitable for the reaction stage according to the invention when everything is retained except the support geometry which is changed to 5 mm×3 mm×1.5 mm (external diameter×length×internal diameter). The multimetal oxides mentioned can also be used in the reaction stage according to the invention in the form of the corresponding unsupported catalyst rings.

It is essential to the invention that the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone.

The volume-specific (i.e. normalized to the unit of the particular bed volume) activity of a fixed bed catalyst zone can then be adjusted over the fixed catalyst bed zone in a substantially constant manner by starting from a basic amount of shaped catalyst bodies prepared in a uniform manner (their bed corresponds to the maximum achievable volume-specific activity) and homogeneously diluting it in the particular fixed catalyst bed zone with shaped bodies (shaped diluent bodies) which behave substantially inertly with regard to the heterogeneously catalyzed partial gas phase oxidation. The higher the proportion of shaped diluent bodies selected, the less active composition and catalyst activity, present in a certain volume of the bed. Useful materials for such inert shaped diluent bodies are in principle all of those which are suitable as support material for coated catalysts suitable according to the invention.

Useful such materials include, for example, porous or nonporous aluminum oxides, silicon dioxide, thorium dioxide, zirconium dioxide, silicon carbide, silicates such as magnesium silicate or aluminum silicate or the steatite already mentioned above (e.g. Steatite C-220 from CeramTec).

The geometry of such inert shaped diluent bodies may in principle be as desired. In other words, they may, for example, be spheres, polygons, solid cylinders or else rings.

According to the invention, the inert shaped diluent bodies selected will preferably be those whose geometry corresponds to that of the shaped catalyst bodies to be diluted with them.

According to the invention, it is advantageous when the chemical composition of the active composition used does not vary over the entire fixed catalyst bed. In other words, although the active composition used for a single shaped catalyst body can be a mixture of different multimetal oxides comprising the elements Mo and V, the same mixture then has to be used for all shaped catalyst bodies of the fixed catalyst bed.

A volume-specific activity increasing zone by zone over the fixed catalyst bed in the flow direction of the reaction gas mixture can therefore be achieved for the process according to the invention in a simple manner, for example, by beginning the bed in a first fixed catalyst bed zone with a high proportion of inert shaped diluent bodies based on one type of shaped catalyst bodies, and then reducing this proportion of shaped diluent bodies zone by zone in the flow direction.

However, a zone by zone increase in the volume-specific activity is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition, by increasing the proportion of shaped catalyst bodies having higher proportion by weight of active composition zone by zone. Alternatively, the active compositions themselves can be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bed densities (for example, in the case of unsupported catalysts having identical active compositions of the different geometries). It will be appreciated that the variants described can also be used in combination.

It is of course also possible to use mixtures of catalysts having chemically different active compositions and, as a consequence of these different compositions, having different activities for the fixed catalyst bed. These mixtures may in turn, zone by zone, be varied in their composition and/or be diluted with different amounts of inert shaped diluent bodies.

Upstream and/or downstream of the fixed catalyst bed may be disposed beds consisting exclusively of inert material (for example only shaped diluent bodies) (in this document, they are not included for terminology purposes in the fixed catalyst bed, since they contain no shaped bodies which have multimetal oxide active composition). The shaped diluent bodies used for the inert bed can have the same geometry as the shaped catalyst bodies used in the fixed catalyst bed. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having a diameter d=4–5 mm. Temperature zones A and B in the process according to the invention may also extend to the inert beds. According to the invention, it is advantageous when neither temperature zone A nor temperature zone B covers more than three fixed catalyst bed zones (according to the invention, at least one fixed catalyst bed zone is necessarily covered by both temperature zones).

According to the invention, it is particularly advantageous when the entire fixed catalyst bed comprises not more than five, advantageously not more than four or three fixed catalyst bed zones.

According to the invention, at the transition from one fixed catalyst bed zone to another fixed catalyst bed zone (in the flow direction of the reaction gas mixture), the volume-specific active composition (i.e. the weight of the multimetal oxide active composition present in the uniform bed volume) should (in the case of uniform active composition over the entire fixed catalyst bed) advantageously increase by at least 5% by weight, preferably by at least 10% by weight (this applies in particular in the case of uniform shaped catalyst bodies over the entire fixed catalyst bed). In general, this increase in the process according to the invention will not be more than 50% by weight, usually not more than 40% by weight. According to the invention, in the case of uniform active composition over the entire fixed catalyst bed, the difference in the volume-specific active composition of the fixed catalyst bed zone having the lowest volume-specific activity and the fixed catalyst bed zone having the highest volume-specific activity should also advantageously not be more than 50% by weight, preferably not more than 40% by weight, and more preferably not more than 30% by weight.

In the process according to the invention, the fixed catalyst bed will frequently consist of only two fixed catalyst bed zones.

According to the invention, preference is given to the last fixed catalyst bed zone in the flow direction of the reaction gas mixture being undiluted. In other words, it preferably consists exclusively of shaped catalyst bodies. If required, it may also consist of a bed of shaped catalyst bodies whose volume-specific activity is reduced, for example by dilution with inert material, for example by 10%. When the fixed catalyst bed consists of only two fixed catalyst bed zones, it is generally advantageous according to the invention (as is quite generally the case in the process according to the invention) when the fixed catalyst bed zone having the highest volume-specific activity extends into temperature zone A (in particular when the heating is effected in temperature zone A and temperature zone B by means of a flowing heat carrier which in each case flows in countercurrent to the reaction gas mixture).

When the fixed catalyst bed consists of only three fixed catalyst bed zones, it is generally equally advantageous according to the invention when the fixed catalyst bed zone having the highest volume-specific activity extends into temperature zone A (in particular when the heating in temperature zone A and temperature zone B is effected by means of a flowing heat carrier which in each case flows in countercurrent to the reaction gas mixture).

When the fixed catalyst bed consists of four fixed catalyst bed zones, it is generally advantageous in accordance with the invention when the fixed catalyst bed zone having the second highest volume-specific activity extends both into temperature zone A and into temperature zone B (in particular when temperature zone A and temperature zone B are heated by means of a flowing heat carrier which in each case flows in countercurrent to the reaction gas mixture).

In the case of cocurrent flow of reaction gas mixture and heat carriers in temperature zones A and B, it may be advantageous according to the invention if the fixed catalyst bed zone having the highest volume-specific activity does not extend into temperature zone A but does not have its beginning until beyond the transition from temperature zone A to temperature zone B.

The volume-specific activity between two fixed catalyst bed zones can be differentiated experimentally in a simple manner by passing the same acrolein-containing starting reaction gas mixture over fixed catalyst beds of the same length but each corresponding to the composition of the particular fixed catalyst bed zone under identical boundary conditions (preferably the conditions of the contemplated process). The higher amount of acrolein converted indicates the higher volume-specific activity.

When the total length of the fixed catalyst bed is L, it is advantageous in accordance with the invention if there is no transition from one fixed catalyst bed zone to another fixed catalyst bed zone within the region of $$X \pm L \cdot \frac{4}{100}$$

or within the region of $$X \pm L \cdot \frac{3}{100}$$

or within the region of $$X \pm L \cdot \frac{2}{100}$$

where X is the location within the fixed catalyst bed of the transition from temperature zone A to temperature zone B.

Preference is given in accordance with the invention to the fixed catalyst bed in the process according to the invention being structured as follows in the flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed catalyst bed, a homogeneous mixture or two (having decreasing dilution) successive homogeneous mixtures of shaped catalyst bodies and shaped diluent bodies (both preferably having substantially the same geometry), in which the proportion of shaped diluent bodies is such that the volume-specific active composition, based on a bed consisting only of shaped catalyst bodies, has been reduced by from 10 to 50% by weight, preferably from 20 to 45% by weight and more preferably from 25 to 35% by weight. According to the invention, this first or these first two zones are then advantageously followed to the end of the length of the fixed catalyst bed (i.e., for example, to a length of from 2.00 to 3.00 m, preferably from 2.50 to 3.00 m) by either a bed of the shaped catalyst bodies diluted only to a slighter extent (than in the first or in the first two zones) or, most preferably, an unaccompanied bed of the same shaped catalyst bodies which have also been used in the first zones.

The aforementioned applies in particular when the shaped catalyst bodies used in the fixed catalyst bed are coated catalyst rings or coated catalyst spheres (in particular those which are listed in this document as preferred). For the purposes of the aforementioned structuring, both the shaped catalyst bodies or their support rings and the shaped diluent bodies in the process according to the invention substantially have the ring geometry 7 mm×0.3 mm×4 mm (external diameter×length×internal diameter).

The abovementioned also applies when, instead of inert shaped diluent bodies, shaped coated catalyst bodies are used whose active composition content is from 2 to 15 weight percentage points lower than the active composition content of the shaped coated catalyst bodies at the end of the fixed catalyst bed.

A pure inert material bed whose length, based on the length of the fixed catalyst bed, is advantageously from 5 to 20% generally proceeds the fixed catalyst bed in the flow direction of the reaction gas mixture. It is normally used to heat the reaction gas mixture.

It is advantageous in accordance with the invention if temperature zone A (which also advantageously extends in accordance with the invention to the preliminary bed of inert material) in the abovementioned beds extends for from 5 to 20%, frequently from 5 to 15%, of its length into the last (volume-specifically most active)-fixed catalyst bed zone in the flow direction of the reaction gas mixture.

In an advantageous manner from an application point of view, the reaction stage of the process according to the invention is carried out in a two-zone tube bundle reactor, as described, for example, in DE-A 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for carrying out the first reaction stage of the process according to the invention.

In other words, in the simplest manner, the fixed catalyst bed to be used in accordance with the invention (possibly with downstream and/or upstream inert beds) is disposed in the metal tubes of a tube bundle reactor and two spatially separated heating media, generally salt melts, are conducted around the metal tubes. The tube section over which the particular salt bath extends represents a temperature zone in accordance with the invention.

In other words, in a simple manner, for example, a salt bath A flows around those sections of the tubes (temperature zone A) in which acrolein is oxidatively converted (on single pass) until a conversion value in the range from 45 to 85 mol % (preferably from 50 to 85 mol %, more preferably from 60 to 85 mol %) is achieved, and a salt bath B flows around the section of the tubes (temperature zone B) in which the acrolein is subsequently oxidatively converted (on single pass) until a conversion value of at least 90 mol % is achieved (if required, the temperature zones A, B to be used in accordance with the invention can be followed by further temperature zones which are maintained at individual temperatures).

It is advantageous from an application point of view if the reaction stage of the process according to the invention includes no further temperature zones. In other words, the salt bath B advantageously flows around the section of the tubes in which acrolein is subsequently oxidatively converted (on single pass) up to a conversion value of $\geq 92$ mol %, or $\geq 94$ mol %, or $\geq 96$ mol %, or $\geq 98$ mol % and frequently even $\geq 99$ mol % or more.

Typically, the beginning of the temperature zone B lies beyond the heating point maximum of temperature zone A.

According to the invention, both salt baths A, B can be conducted in cocurrent or in countercurrent through the space surrounding the reaction tubes relative to the flow direction of the reaction gas mixture flowing through the reaction tubes. It will be appreciated that, in accordance with the invention, cocurrent flow may be applied in temperature zone A and countercurrent flow in temperature zone B (or vice versa).

In all of the aforementioned cases, it will be appreciated that a transverse flow can be superimposed on the parallel flow of the salt melt relative to the reaction tubes taking place within the particular temperature zone, so that the individual temperature zone corresponds to a tube bundle reactor as described in EP-A 700714 or in EP-A 700893, which results overall in a meandering flow profile of the heat exchange medium in a longitudinal section through the catalyst tube bundle.

Typically, the catalyst tubes in the aforementioned two-zone tube bundle reactors for the reaction stage according to the invention are manufactured from ferritic steel and typically have a wall thickness of from 1 to 3 mm. Their internal diameter is generally from 20 to 30 mm, frequently from 21 to 26 mm. Their length is advantageously from 3 to 4 m, preferably 3.5 m. In each temperature zone, the fixed catalyst bed occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5 000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (the catalyst tube pitch) is from 35 to 45 mm (cf. EP-B 468290).

Useful heat exchange media are in particular fluid heating media. It is particularly advantageous to use melts of salts such as potassium nitrate, potassium nitrite, sodium-nitrite and/or sodium nitrate, or of low-melting metals such as sodium, mercury and also alloys of different metals.

In general, in all of the abovementioned flow arrangements in the two-zone tube bundle reactors of the reaction stage according to the invention, the flow rate within the two heat exchange medium circuits required is selected in such a way that the temperature of the heat exchange medium rises from the entrance into the temperature zone to the exit from the reaction zone by from 0 to 15° C. In other words, the aforementioned AT may be from 1 to 10° C., or from 2 to 8° C., or from 3 to 6° C., in accordance with the invention.

According to the invention, the entrance temperature of the heat exchange medium into temperature zone A is normally in the range from 230 to 320° C., preferably in the range from 250 to 300° C. and more preferably in the range from 260 to 280° C. According to the invention, in the case of acrolein catalyst velocities on the fixed catalyst bed of $\geq 70$ l (STP)/l·h and $\leq 150$ l (STP)/l·h, the entrance temperature of the heat exchange medium into reaction zone B is likewise normally in the range from 230 to 320° C. or 280° C., but at the same time normally, advantageously in accordance with the invention, from $\geq 0$° C. to $\leq 20$° C. or $\leq 10$° C., or $\geq 0$° C. and $\leq 5$° C., or frequently $\geq 0$° C. and $\leq 3$° C., below the entrance temperature of the heat exchange medium entering reaction zone A. According to the invention, in the case of acrolein hourly space velocities on the fixed catalyst bed of $\geq 150$ l (STP)/l·h and (generally) $\leq 300$ l (STP)/l·h (or 600 l (STP)/l·h), the entrance temperature of the heat exchange medium into temperature zone B will likewise be in the range from 230 to 320° C., but at the same time normally, advantageously in accordance with the invention, from $>0$° C. and $\leq 40$° C., or $\geq 5$° C. and $\leq 35$° C. or $\leq 30$° C. or $\geq 10$° C. and $\leq 25$° C. or $\leq 20$° C., or 15° C. above the entrance temperature of the heat exchange medium entering temperature zone A.

It is pointed out once again at this juncture that, for an implementation of the reaction stage according to the invention of the process according to the invention, it is also possible to use in particular the two-zone tube bundle reactor type described in DE-B 2201528 which includes the possibility of removing a portion of the hotter heat exchange medium of reaction zone B to reaction zone A, in order to optionally heat a cold starting reaction gas mixture or a cold cycle gas. The tube bundle characteristics within an individual temperature zone may also be configured as described in EP-A 382098.

Normally, acrolein is used in the process according to the invention which has been obtained by catalytic gas with oxidation of propene. In general, the acrolein-containing reaction gases of this propene oxidation are used without intermediate purification, which is why the starting reaction gas mixture according to the invention can also comprise small amounts of, for example, unconverted propene or by-products of the propene oxidation. Normally, the oxygen required for the acrolein oxidation also has to be added to the product gas mixture of the propene oxidation.

Advantageously, such catalytic oxidation of propene to acrolein in the gas phase preceding the process according to the invention is carried out in a similar manner to the process according to the invention.

In other words, to carry out the process according to the invention, two two-zone tube bundle reactors can be connected in series or combined to give a four-zone tube bundle reactor, as described, for example, in WO 01/36364 and the propene oxidation is carried out in the first two-zone portion and the acrolein oxidation according to the invention in the second two-zone portion.

Normally, in the second case, an inner bed is disposed between the fixed catalyst beds for the two reaction stages. However, such an intermediate inert bed can also be dispensed with.

Of course, the propene oxidation stage can also be a separate one-zone tube bundle reactor or one which has been combined in an appropriate manner with the subsequent acrolein oxidation stage.

In the event of combination, the length of the reaction tubes in many cases corresponds to the sum of the lengths of the uncombined tube bundle reactors.

The propene content in the starting reaction gas mixture in the process according to the invention can, for example, be at values of from 4 to 15% by volume, frequently from 5 to 12% by volume, or from 5 to 8% by volume (based in each case on the total volume).

Frequently, the process according to the invention will be carried out as a propene:oxygen:inert gases (including steam) volume ratio in the starting reaction gas mixture of 1:(1.4 to 2.3):(5 to 25), preferably 1:(1.4 to 2.3):(10 to 15). In general, at least 20% of the volume of the inert gas will consist of molecular nitrogen. However, $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of the inert gas may consist of molecular nitrogen (in this document, inert diluent gases generally refer to those of which less than 5%, preferably less than 2%, is converted on single pass through the particular reaction stage; in addition to molecular nitrogen, these are, for example, gases such as propane, ethane, methane, pentane, butane, $CO_2$, CO, steam and/or noble gases). Up to 50 mol %, or up to 75 mol % and more of the inert diluent gas in the process according to the invention can consist of propane. Cycle gas, as remains after the removal of the acrylic acid from the product gas mixture, can also be a constituent of the diluent gas.

The catalysts for such a catalytic propene oxidation in the gas phase are in particular those of EP-A 15565, EP-A 575897, DE-A 19746210 and DE-A 19855913.

The inert gas to be used in the process according to the invention may consist of $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, or molecular nitrogen.

Advantageously, the inert diluent gas in the process according to the invention will consist of from 5 to 20% by weight of $H_2O$ and from 70 to 90% by volume of $N_2$.

At acrolein hourly space velocities of above 250 l (STP)/ l·h, the use of inert diluent gases (inert diluent gases are generally those of which less than 5%, preferably less than 2%, are converted on single pass) such as propane, ethane, methane, butane, pentane, $CO_2$, CO, steam and/or noble gases is recommended. It will be appreciated that these gases can also be used at lower hourly space velocities. It is also possible to use an inert gas consisting of only one or more than one of the abovementioned gases.

Normally, the acrolein hourly space velocity in the process according to the invention will not exceed the value of 600 l (STP)l·h.

Useful sources for the molecular oxygen required in the process according to the invention are both air and air depleted of molecular nitrogen (e.g. $\geq 90\%$ by volume of $O_2$, $\leq 10\%$ by volume of $N_2$).

The acrolein content in the starting reaction gas mixture for the process according to the invention can have, for example, values of from 3 to 15% by volume, frequently from 4 to 10% by volume or from 5 to 8% by volume (based in each case on the total volume).

Frequently, the process according to the invention will be performed at an acrolein:oxygen:steam:inert gas volume ratio (l (STP)) present in the starting reaction gas mixture of 1:(1 to 3):(0 to 20):(3 to 30), preferably of 1:(1 to 3):(0.5 to 10):(7 to 10).

It will be appreciated that the process according to the invention can also be carried out at an acrolein:oxygen: steam:others volume ratio present in the starting reaction gas mixture (l (STP)) of 1:(0.9 to 1.3):(2.5 to 3.5):(10 to 12).

It is emphasized at this juncture that the multimetal oxide compositions of DE-A 10261186 are also advantageous for the fixed catalyst bed of the process according to the invention.

Designs of a two-zone tube bundle reactor for a propene partial oxidation stage preceding the reaction stage according to the invention which are advantageous in accordance with the invention can have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

Catalyst tubes:

material of the catalyst tubes: ferritic steel;

dimensions of the catalyst tubes: length, for example, 3 500 mm;

external diameter, for example, 30 mm;

wall thickness, for example, 2 mm;

number of catalyst tubes in the tube bundle: for example, 30 000, or 28 000, or 32 000, or 34 000; in addition up to 10 thermal tubes (as described in EP-A 873 783 and EP-A 12 70 065) which are charged in the same way as the catalyst tubes (in a spiral manner rotating from the very outside toward the inside), for example of the same length and wall thickness but having an external diameter of, for example, 33.4 mm and a centered thermowell of external diameter, for example, 8 mm and wall thickness of, for example, 1 mm;

reactor (same material as the catalyst tubes):

cylindrical vessel of internal diameter 6 000–8 000 mm;

reactor hoods plated with stainless steel of the type 1.4541; plating thickness: a few mm;

annularly arranged tube bundle, for example with free central space:

diameter of the free central space: for example, 1 000–2 500 mm (for example 1 200 mm, or 1 400 mm, or 1 600 mm, or 1 800 mm, or 2 000 mm, or 2 200 mm, or 2 400 mm);

normally homogeneous catalyst tube pitch in the tube bundle (6 equidistant adjacent tubes per catalyst tube), arrangement in an equilateral triangle, catalyst tube pitch (separation of the central internal axes of immediately adjacent catalyst tubes): 35–45 mm, for example 36 mm, or 38 mm, or 40 mm, or 42 mm, or 44 mm;

the catalyst tubes are secured and sealed by their ends in catalyst tube plates (upper plate and lower plate each having a thickness, for example, of 100–200 mm) and open at their upper ends into a hood joined to the vessel which has an inlet for the starting reaction gas mixture; a separating plate of thickness 20–100 mm disposed, for example, at half the catalyst tube length, divides the reactor space symmetrically into two temperature zones A' (upper zone) and B' (lower zone); each temperature zone is divided into 2 equidistant longitudinal sections by deflecting plates;

the deflecting plate preferably has annular geometry; the catalyst tubes are advantageously secured and sealed at the separating plate; they are not secured and sealed at the deflecting plates, so that the transverse flow rate of the salt melt within one zone is very constant;

each zone is provided with salt melt as a heat carrier by its own salt pump; the feed of the salt melt is, for example, below the deflecting plate and the withdrawal is, for example, above the deflecting plate;

a substream is, for example, removed from both salt melt circuits and cooled, for example, in one common or two separate indirect heat exchangers (steam generation);

in the first case, the cooled salt melt stream is divided, combined with the particular residual stream and pressurized into the reactor by the particular pump into the appropriate annular channel which divides the salt melt over the circumference of the vessel;

the salt melt reaches the tube bundle through the window disposed in the reactor jacket; the flow is, for example, in a radial direction to the tube bundle;

in each zone, the salt melt flows around the catalyst tubes as dictated by the deflection plate, for example in the sequence
 from the outside inward,
 from the inside outward;

the salt melt flows through a window mounted around the circumference of the vessel and collects at the end of each zone in an annular channel disposed around the reactor jacket, in order to be pumped in a circuit including substream cooling;

the salt melt is conducted from bottom to top through each temperature zone.

The reaction gas mixture leaves the reactor of the reaction stage connected upstream of the reaction stage according to the invention at a temperature a few degrees higher than the salt bath entrance temperature of said reactor. For further processing, the reaction gas mixture is advantageously cooled to from 220° C. to 280° C., preferably from 240° C. to 260° C., in a separate aftercooler which is connected downstream of this reactor.

The aftercooler is generally flanged on below the lower tube plate and normally consists of tubes of ferritic steel. Stainless steel sheet metal spirals which may be partly of fully wound are advantageously introduced into the interior of the tubes of the aftercooler, in order to improve the heat transfer.

Salt melt:

The salt melt used may be a mixture of 53% by weight of potassium nitrate, 40% by weight of sodium nitrite and 7% by weight of sodium nitrate; both reaction zones and the aftercooler advantageously use a salt melt of the same composition; the amount of salt pumped by circulation in the reaction zones may be approx. 10 000 m$^3$/h per zone.

Flow control:

The starting reaction gas mixture for propene oxidation advantageously flows from top to bottom through the reactor, while the salt melts having different temperatures of the individual zones are advantageously conveyed from bottom to top;

Catalyst tube and thermal tube charge (from top to bottom), for example:

Section 1: length 50 cm
 steatite rings of geometry 7 mm×7 mm×4 mm (external diameter×length×internal diameter) as a preliminary bed.

Section 2: length 140 cm
 catalyst charge of a homogeneous mixture of 30% by weight of steatite rings of geometry 5 mm×3 mm×2 mm (external diameter×length×internal diameter) and 70% by weight of unsupported catalyst from section 3.

Section 3: length 160 cm catalyst charge of annular (5 mm×3 mm×2 mm=external diameter×length×internal diameter) unsupported catalyst according to example 1 of DE-A 10046957 (stoichiometry: $[Bi_2W_2O_9 \times 2\ WO_3]_{0.5}\ [Mo_{12}CO_{5.5}Fe_{2.94}Si_{1.59}K_{0.08}O_x]_1)$.

Configurations of a two-zone tube bundle reactor for the acrolein reaction stage according to the invention which are advantageous in accordance with the invention can be designed as follows:

Everything as in the two-zone tube bundle reactor for the propene reaction stage. However, the thickness of the upper and lower catalyst tube plates is frequently 100–200 mm, for example 110 mm, or 130 mm, or 150 mm, or 170 mm, or 190 mm.

The aftercooler is dispensed with; instead, the openings of the catalyst tubes open into a hood which is connected to the vessel at the lower end and has an outlet for the product gas mixture; the upper temperature zone is zone A and the lower temperature zone is zone B. Between the outlet "aftercooler" and the inlet "reactor for the reaction stage according to the invention" is advantageously a means for feeding compressed air.

The catalyst tube and thermal tube charge (from top to bottom) can, for example, be as follows:

Section 1: length 20 cm
 steatite rings of geometry 7 mm×7 mm×4 mm (external diameter×length×internal diameter) as a preliminary bed.

Section 2: length 90 cm
 catalyst charge of a homogeneous mixture of 30% by weight of steatite rings of geometry 7 mm×3 mm×4 mm (external diameter×length×internal diameter) and 70% by weight of coated catalyst from section 4.

Section 3: length 50 cm
 catalyst charge of a homogeneous mixture of 20% by weight of steatite rings of geometry 7 mm×3 mm×4 mm (external diameter×length×internal diameter) and 80% by weight of coated catalyst from section 4.

Section 4: length 190 cm
 catalyst charge of annular (7 mm×3 mm×4 mm=external diameter×length×internal diameter) coated catalyst according to preparative example 5 of DE A 10046928 (stoichiometry: $Mo_{12}V_3W_{1.2}Cu_{2.4}O_x$).

Alternatively, the propene stage catalyst tube and thermal tube charge (from top to bottom) can also have the following appearance:

Section 1 length 50 cm
 steatite rings of geometry 7 mm×7 mm×4 mm (external diameter×length×internal diameter) as a preliminary bed.

Section 2: length 300 cm
 Catalyst charge of annular (5 mm×3 mm×2 mm=external diameter×length×internal diameter) unsupported catalyst according to example 1 of DE-A 10046957 (stoichiometry: $[Bi_2W_2O_9 \times 2WO_3]_{0.5} \circ [Mo_{12}Co_{5.6}Fe_{2.94}Si_{1.59}K_{0.08}O_x]_1$).

The acrolein stage catalyst tube and thermal tube charge can also have the following appearance (from top to bottom):

Section 1: length 20 cm
   steatite rings of geometry 7 mm×7 mm×4 mm (external diameter×length×internal diameter) as a preliminary bed.

Section 2: length 140 cm
   catalyst charge of a homogeneous mixture of 25% by weight of steatite rings of geometry 7 mm×3 mm×4 mm (external diameter×length×internal diameter) and 75% by weight of coated catalyst from section 3.

Section 3: length 190 cm
   catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

In all the propene stage charges mentioned, the unsupported catalyst from example 1 of DE-A 10046957 can also be replaced by:
a) a catalyst according to example 1c of EP-A 15565 or a catalyst to be prepared in accordance with this example, except having the active composition $Mo_{12}Ni_{6.5}Zn_2Fe_2Bi_1P_{0.0065}K_{0.06}O_x \circ 10\ SiO_2$;
b) example No. 3 of DE-A 19855913 as an unsupported hollow cylinder catalyst of geometry 5 mm×3 mm×2 mm or 5 mm×2 mm×2 mm;
c) unsupported multimetal oxide II catalyst according to example 1 of DE-A 19746210;
d) one of the coated catalysts 1, 2 and 3 of DE-A 10063162, except applied in the same coating thickness to support rings of geometry 5 mm×3 mm×1.5 mm 7 mm×3 mm×1.5 mm;
e) a coated catalyst according to the exemplary embodiments of DE-A 19815281, except applied in the same coating thickness support rings of geometry 7 mm×3 mm×4 mm, or 8 mm×6 mm×4 mm (external diameter× length×internal diameter).

In the above list, the support material used is preferably steatite C220 from CeramTec.

In all the abovementioned acrolein stage charges according to the invention, the coated catalyst can be replaced in accordance with preparative example 5 of DE-A 10046928:
a) coated catalyst S1 or S7 from DE-A 4442346 having an active composition content of 27% by weight and a coating thickness of 230 μm;
b) a coated catalyst according to examples 1 to 5 of DE 19815281, except applied to support rings of geometry 7 mm×3 mm×4 mm having an active composition content of 20% by weight;
c) coated catalyst having biphasic active composition of stoichiometry $(Mo_{10.4}V_3W_{1.2}O_x)\ (CuMo_{0.5}W_{0.5}O_4)_{1.6}$, prepared according to DE-A 19736105 and having an active composition content of 20% by weight, applied to the abovementioned 7 mm×3 mm×4 mm support.

The fixed catalyst bed for the propane oxidation stage and the fixed catalyst bed for the acrolein oxidation stage according to the invention are advantageously otherwise selected in such a way (for example by dilution with, for example, inert material) that the temperature difference between the heating point maximum of the reaction gas mixture in the individual reaction zones and the particular temperature of the reaction zone generally does not exceed 80° C. This temperature difference is usually ≦70° C., frequently from 20 to 70° C., and this temperature difference is preferably small. For safety reasons, these fixed catalyst beds are also selected in a manner known per se to those skilled in the art (for example by dilution with, for example, inert material) in such a way that the peak-to-salt-temperature sensitivity as defined in EP-A 1106598 is ≦9° C., or ≦7° C., or ≦5° C., or ≦3° C.

Aftercooler and reactor for the acrolein reaction stage are connected by a connecting tube whose length is less than 25 m.

In the examples which follow and also in the reactor arrangement above, the annular shaped diluent bodies and the annular shaped catalyst bodies in the acrolein reaction stage can also be replaced by spherical shaped diluent bodies and spherical shaped catalyst bodies (each having a radius from 2 to 5 mm and having an active composition content of from 10 to 30% by weight, frequently from 10 to 20% by weight).

EXAMPLES

A reaction tube (V2A steel, external diameter 30 mm, wall thickness 2 mm, internal diameter 26 mm, length: 350 cm, and also a thermal tube (external diameter 4 mm) centered in the middle of the reaction tube to receive a thermal element which can be used to determine the temperature in the reaction tube over its entire length) is charged from top to bottom as follows:

Section 1: length 20 cm
   steatite rings of geometry 7 mm×7 mm×4 mm (external diameter×length×internal diameter) as a preliminary bed.

Section 2: length 90 cm
   catalyst charge of a homogeneous mixture of 30% by weight of steatite rings of geometry 7 mm×3 mm×4 mm (external diameter×length×internal diameter) and 70% by weight of coated catalyst from section 4.

Section 3: length 50 cm
   catalyst charge of a homogeneous mixture of 20% by weight of steatite rings of geometry 7 mm×3 mm×4 mm (external diameter×length×internal diameter) and 80% by weight of coated catalyst from section 4.

Section 4: length 190 cm
   catalyst charge of annular (7 mm×3 mm×4 mm=external diameter×length×internal diameter) coated catalyst according to preparative example 5 of DE A 10046928 (stoichiometry: $Mo_{12}V_3W_{1.2}Cu_{2.4}O_x$).

The first 175 cm from top to bottom are thermostatted by means of a salt bath C pumped in countercurrent. The second 175 cm are thermostatted by means of a salt bath D pumped in countercurrent.

Gas phase oxidation:
The above-described reaction tube is continuously charged with a starting reaction gas mixture 1 of the following composition, and the loading and the thermostatting of the reaction tube are varied:
   5.5% by volume of acrolein,
   0.3% by volume of propene,
   6.0% by volume of molecular oxygen,
   0.4% by volume of CO,
   0.8% by volume of $CO_2$,
   9.0% by volume water, and
   78.0% by volume of nitrogen.

The reaction gas mixture flows through the reaction tube from top to bottom.

The pressure at the entrance to the reaction tube varies between 1.6 and 2.1 bar as a function of the acrolein hourly space velocity.

A small sample is taken from the product gas mixture at the reaction tube exit for gas chromatography analysis. At the end of reaction zone A, there is likewise an analysis point.

The results as a function of hourly space velocities and salt bath temperatures are shown by the following table 1 (the letter E in brackets means example).

$T_A, T_B$, are the temperatures of the salt baths circulated by pumping in the reaction zones A and B in ° C.

$C_A^{AC}$ is the propene conversion at the end of reaction zone A in mol %.

$C_B^{AC}$ is the propene conversion at the end of reaction zone B in mol %.

$S^{AA}$ is the selectivity of acrylic acid formation in the product gas mixture based on converted acrolein in mol %.

$T^{maxA}$, $T^{maxB}$ are the highest temperature of the reaction gas mixture within the reaction zones A and B in ° C.

TABLE 1

| Acrolein hourly space velocity (I (STP)/I · h) | $T_A$ | $T_B$ | $T^{maxA}$ | $T^{maxB}$ | $C_A^{AC}$ | $C_B^{AC}$ | $S^{AA}$ |
|---|---|---|---|---|---|---|---|
| 106 (E) | 260 | 260 | 302 | 276 | 80.7 | 99.3 | 95.4 |
| 108 (E) | 262 | 259 | 312 | 275 | 84.8 | 99.3 | 95.8 |
| 152 (E) | 263 | 269 | 303 | 287 | 78.8 | 99.3 | 95.8 |

COMPARATIVE EXAMPLES

Everything is carried out as in the examples. However, the length of the charging sections of the fixed catalyst bed is changed as follows:

Section 3: 65 cm instead of 50 cm

Section 4: 175 cm instead of 190 cm.

The results are shown by Table 2. (C) means comparative example

TABLE 2

| Acrolein hourly space velocity (I (STP)/I · h) | $T_A$ | $T_B$ | $T^{maxA}$ | $T^{maxB}$ | $C_A^{AC}$ | $C_B^{AC}$ | $S^{AA}$ |
|---|---|---|---|---|---|---|---|
| 103 (C) | 265 | 260 | 323 | 276 | 80.8 | 99.3 | 95.2 |
| 106 (C) | 268 | 259 | 332 | 275 | 84.9 | 99.2 | 95.0 |
| 150 (C) | 267 | 269 | 326 | 287 | 78.6 | 99.3 | 95.3 |

In comparison with the results in Table 1, lower $S^{AA}$ are achieved at comparable $C_B^{AC}$ values.

We claim:

1. A process for partially oxidizing acrolein to acrylic acid in the gas phase under heterogeneous catalysis by conducting a starting reaction gas mixture comprising acrolein, molecular oxygen and at least one inert gas, and contains the molecular oxygen and the acrolein in a molar $O_2:C_3H_4O$ ratio of $\geq 0.5$ in a reaction stage over a fixed catalyst bed whose active composition is at least one multimetal oxide comprising the elements Mo and V, in such a way that
   the fixed catalyst bed is arranged in two spatially successive temperature zones A, B,
   both the temperature of temperature zone A and the temperature of temperature zone B are a temperature in the range from 230 to 320° C.,
   the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone,
   the temperature zone A extends up to a conversion of the acrolein of from 45 to 85 mol %,
   on single pass of the starting reaction gas mixture through the entire fixed catalyst bed, the acrolein conversion is $\geq 90$ mol % and the selectivity of acrylic acid formation based on converted acrolein is $\geq 90$ mol %,
   the sequence in time in which the reaction gas mixture flows through the temperature zones A, B corresponds to the alphabetic sequence of the temperature zones,
   the hourly space velocity of the acrolein contained in the starting reaction gas mixture on the fixed catalyst bed is $\geq 70$ l (STP) of acrolein/l of fixed bed catalyst · h, and
   the difference $T^{maxA}-T^{maxB}$, formed from the highest temperature $T^{maxA}$ which the reaction gas mixture has within temperature zone A, and the highest temperature $T^{maxB}$ which the reaction gas mixture has within temperature zone B is $\geq 0°$ C.,
   wherein the transition from temperature zone A to temperature zone B in fixed catalyst bed does not coincide with a transition from one fixed catalyst bed zone to another fixed catalyst bed zone.

2. A process as claimed in claim 1, wherein $T^{maxA}-T^{maxB}$ is $\geq 3°$ C. and $\leq 60°$ C.

3. A process as claimed in claim 1, wherein $T^{maxA}-T^{maxB}$ is $\geq 5°$ C. and $\leq 40°$ C.

4. A process as claimed in claim 1, wherein the acrolein hourly space velocity on the fixed catalyst bed is $\geq 70$ l (STP)/l·h and <150 l (STP)/l·h.

5. A process as claimed in claim 1, wherein the propene hourly space velocity on the fixed catalyst bed is $\geq 150$ l (STP)/l·h and $\leq 300$ l (STP)/l·h.

6. A process as claimed in claim 1, wherein the temperature of reaction zone A is from 250 to 300° C.

7. A process as claimed in claim 1, wherein the temperature of reaction zone A is from 260 to 280° C.

8. A process as claimed in claim 1, wherein temperature zone A extends to an acrolein conversion of from 50 to 85 mol %.

9. A process as claimed in claim 1, wherein temperature zone A extends to an acrolein conversion of from 60 to 85 mol %.

10. A process as claimed in claim 1, wherein the $O_2$: acrolein ratio in the starting reaction gas mixture is $\geq 1$.

11. A process as claimed in claim 1, wherein the chemical composition of the active composition used is unchanged over the entire fixed catalyst bed.

12. A process as claimed in claim 1, wherein the entire fixed catalyst bed comprises not more than 4 fixed catalyst bed zones.

13. A process as claimed in claim 1, wherein, when the active composition is uniform over the entire fixed catalyst bed, the volume-specific active composition in the flow direction of the reaction gas mixture increases by at least 5% by weight at the transition from one fixed catalyst bed zone to another fixed catalyst bed zone.

14. A process as claimed in claim 1, wherein, when the active composition is uniform over the entire fixed catalyst bed, the volume-specific active composition in the flow direction of the reaction gas mixture increases by at least 10% by weight at the transition from one fixed catalyst bed zone to another fixed catalyst bed zone.

15. A process as claimed in claim 1, wherein, when the active composition is uniform over the entire fixed catalyst bed, the difference in the volume-specific active composition between the fixed catalyst bed zone having the lowest volume-specific activity and the fixed catalyst bed zone having the highest volume-specific activity is not more than 40% by weight.

16. A process as claimed in claim 1, wherein the last fixed catalyst bed zone in the flow direction of the reaction gas mixture is undiluted and consists only of shaped catalyst bodies.

17. A process as claimed in claim 1, wherein the fixed catalyst bed zone having the highest volume-specific activity extends into temperature zone A.

18. A process as claimed in claim 1, wherein the fixed catalyst bed consists of four fixed catalyst bed zones and the fixed catalyst bed zone with the second highest volume-specific activity extends both into temperature zone A and into temperature zone B.

19. A process as claimed in claim 1, wherein there is no transition from one fixed catalyst bed zone to another fixed catalyst bed in the fixed catalyst bed within the range of $X \pm L \cdot 4/100$ where L is the length of the fixed catalyst bed and X is the point within the fixed catalyst bed of transition from temperature zone A to temperature zone B.

* * * * *